United States Patent [19]
Malen et al.

[11] 4,378,366
[45] Mar. 29, 1983

[54] 2-[TRIFLUOROETHYLAMINE]OXAZO-LINES

[75] Inventors: Charles Malen, Fresnes; Pierre Roger, Trappes; Michel Laubie, Vaucresson, all of France

[73] Assignee: Science Union et Cie, Suresnes, France

[21] Appl. No.: 295,255

[22] Filed: Aug. 24, 1981

Related U.S. Application Data

[63] Continuation of Ser. No. 102,825, Dec. 12, 1979, abandoned.

[30] Foreign Application Priority Data

Dec. 20, 1978 [FR] France ............................... 78 35741

[51] Int. Cl.³ .................... C07D 263/16; A61K 31/42
[52] U.S. Cl. ..................................... 424/272; 548/233
[58] Field of Search ........................ 548/233; 424/272

[56] References Cited

U.S. PATENT DOCUMENTS 3,988,464 10/1976 Malen et al. ......................... 548/233
4,102,890 7/1978 Malen et al. ......................... 548/233

OTHER PUBLICATIONS

Malen et al., "Chem. Abstracts", vol. 81, (1974), #105533b.
Yale, "Jou. of Medicinal and Pharmaceutical Chemistry", vol. #2, (1959), pp. 121–133.

Primary Examiner—Anton H. Sutto
Attorney, Agent, or Firm—Gordon W. Hueschen

[57] ABSTRACT

This invention relates to trifluorethylamines and to a process for producing the same.

These trifluorethylamines are substituted on the nitrogen atom with a lower alkyl or a cyclo lower alkyl radical.

They are endowed with interesting pharmacological properties.

11 Claims, No Drawings

2-[TRIFLUOROETHYLAMINE]OXAZOLINES

This is a continuation of application Ser. No. 102,825, filed Dec. 12, 1979, now abandoned.

PRIOR ART

The prior art may be illustrated by the following references

U.S. Pat. No. 4,102,890 (to the same assignee)

U.S. patent application No. (to the same assignee) 866,220 filed on Jan. 3rd, 1978 now abandoned U.S. patent application No. (to the same assignee) 031,386 filed on Apr. 19, 1979 now U.S. Pat. No. 4,267,345, issued May 12, 1981.

This invention relates to novel trifluoroethylamines, the nitrogen atom of which is substituted and to processes for producing the said compounds.

More particularly this invention relates to trifluoroethylamines the nitrogen atom of which is substituted with a nitrogen-containing a heterocyclic ring.

Specifically this invention provides as new compounds the N-substituted trifluoroethylamines of the formula I

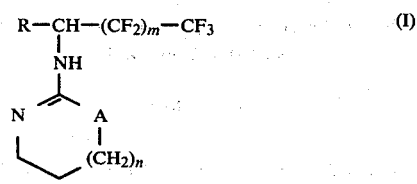

Wherein R is a lower alkyl radical having from 1 to 6 carbon atoms in straight or branched chain, a lower cycloalkyl radical having from 3 to 7 carbon atoms which maybe substituted by one or more lower alkyl radicals, or lower alkoxy radicals.

A is an oxygen, a sulphur atom or an imino group n is zero or an integer of 1 to 2 m is zero or 1

This invention also provides the acid addition salts of a compound of formula I with a mineral or organic acid, preferably a therapeutically-compatible acid.

Due to their chemical structure, the compounds of formula I have at least one asymetric carbon and consequently they may be either in the racemic form or in an optically-active form. The optically-active isomers as well as the racemic mixtures are part of this invention.

Further when R is an unsubstituted or substituted cycloalkyl radical, the molecule includes at least one extra asymetric carbon atom and the resulting compounds may be separated into their diastereoisomeric forms cis or trans. Each of the diastereoisomeric compounds may be split into their enantiomers i.e. the laevorotatory and the dextrorotatory derivatives.

As presently preferred compounds, they may be cited:

(a) the oxazolines of formula $I_A$

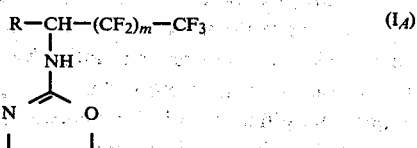

Wherein R and m have the previously-given definitions, and specifically:

dl 2-[(1-trifluoromethyl 3-methyl)butylamino]oxazoline and its hydrochloric acid addition salt 2-[(1-trifluoromethyl 1-cyclohexyl)methylamino]oxazoline (dextrorotatory isomer)

2-[(1-trifluoromethyl 1-cyclohexyl)methylamino]oxazoline (laevorotatory isomer)

dl 2-[(1-trifluoromethyl)(4'-methylcyclohexyl-1')methylamino]oxazoline (b) the imidazolines of formula $I_B$

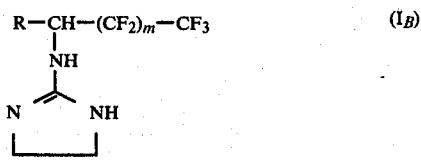

Wherein R and m have the above-specified definitions and specifically 2-[(1-trifluoromethyl 1-cyclohexyl)methylamino]imidazoline (c) the thiazolines of formula $I_C$

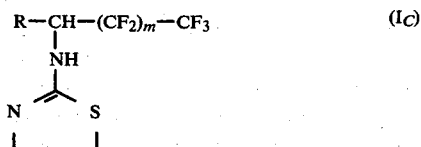

Wherein R and m have the above-specified definitions and specifically 2-[(1-trifluoromethyl 1-cyclohexyl)methylamino]thiazoline (d) the tetrahydropyrimidines of formula $I_D$

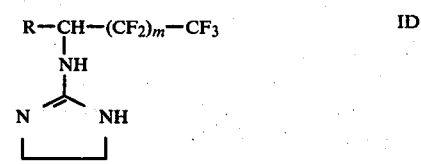

in which R and m have the above-specified definitions and specifically dl 2-[(1-trifluoromethyl 1-cyclohexyl)-methylamino]tetrahydropyimidine As far as this invention is concerned, the term lower alkyl radical encompasses the hydrocarbon straight or branched chains having from 1 to 6 carbon atoms such as methyl, ethyl, isopropyl, neopentyl, tertbutyl or n-hexyl. This chain may be substituted with a hydroxy, a lower acyloxy, a lower alkoxy or a diethylaminogroup. Examples of such substituted lower alkyl groups are β-ethoxyethyl, γ-hydroxybutyl or diethylaminopropyl.

A lower alkoxy has from 1 to 6 carbon atoms. Examples of suitable alkoxy are methoxy, ethoxy, isopropoxy, secbutyloxy, neopentyloxy, tertbutyloxy, β-ethoxy β-ethoxy or dimethylaminoethoxy.

As a cycloalkyl radical, it has to be understood it has from 3 to 7 ring atoms which may be substituted with one to three substituents selected from the group consisting of lower alkyl radicals and lower alkoxy radicals. Examples of such cycloalkyl radicals are the cyclopropyl radical, 2,2-dimethyl cyclopropyl, 1-tertbutylcyclopropyl-I radical, cyclobutyl, cyclopentyl, cyclohexyl, 2,6-dimethylcyclohexyl, 3,4,5-trimethoxycyclohexyl or the cycloheptyl radical.

The compounds of formula I may be added to mineral or organic acids and thus easily form acid addition salts. Examples of acids which may be conveniently added are hydrochloric acid, hydrobromic acid, phosphoric, sulphuric acid, nitric acid, metaphosphoric acid, or thiosulphuric acid, formic acid, acetic acid, di n-propylacetic acid, tartaric acid, citric acid, maleic acid, fumaric acid, itaconic acid, benzoic acid, glucose 1-phosphoric acid, glucose 1,6-diphosphoric acid, methanesulphonic acid, ethane sulphonic acid, isethionic acid or benzene sulphonic acid, thiazol 5-carboxylic acid, nipecotic acid.

The compounds of formula I are endowed with interesting pharmacological properties, namely with antihypertensive properties. They induce only very slight effects on the Central Nervous System. They may be used as a drug for treating hypertension without fear of noxious side-effects such as state of sedation, tendency to sleepiness or analgesia. The acid addition salts thereof may be utilized as well as the free bases.

This invention also extends to the pharmaceutical compositions incorporating as active ingredient at least one compound of formula I or an acid addition salt thereof in conjunction or admixture with an inert non-toxic pharmaceutically-acceptable carrier or vehicle.

These pharmaceutical compositions may also incorporate a further active ingredient having a similar therapeutic activity, a complementary or a synergistic therapeutic activity.

Examples of complementary therapeutic agents are the diuretics such as a thiazide or a sulfamide for example Furosemide [5-(aminosulfonyl)-4-chloro-2-[2-(furanylmethyl)amino]benzoic acid], hydrochlorothiazide [6-chloro-3,4-dihydro-2H-1,2,4-benzothiadiazine-7-sulfonamide-1,1-dioxide] or Indapamide [3-(aminosulfonyl)-4-chloro-N-(2,3-dihydro-2-methyl-1H-indol-1-yl)benzamide]; Anti-aldosterone agents may also be added such as Canrenone (17-hydroxy-3-oxo-17α-(2-carboxyethyl)-17-β-hydroxyandrosta-4,6-dien-3-one lactone) or potassium Canrenoate.

The pharmaceutical compositions are those suitable for parenteral, oral, sublingual, percutaneous or rectal way of administration. Suitably they may be the coated or uncoated tablets, the capsules, the soft gelatine capsules, the dragees, the pills, the drinkable emulsions or solutions, the drops, the syrups or the jellies; the the injectible solutions or suspensions packed in ampuls, multidoses flasks, vials, or autoinjectible syrups; the solutions in a polar solvent for percutaneous applications; the sublingual tablets or the suppositories.

The useful dosology may broadly vary depending on the age of the patient, the weight of the patient, the route of administration and the severity of the disease. In human therapy the dosology preferably ranges from 1 mg to 2 mg per unit dosage and the daily dose ranges from 1 mg to 5 mg in the men. In veterinary medicine the dosology will be determined on a weight basis.

This is another object of this invention to provide a process for producing the N-substituted trifluoroethylamines of formula I.

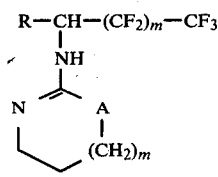

wherein R is a lower alkyl radical or a lower cycloalkyl radical.

A is an oxygen, a sulphur atom or an imino group.

n is zero or an integer of 1 to 2 m is zero or one which comprises the steps of reacting a trifluoroethylamine of formula II in a racemic or optically-active form

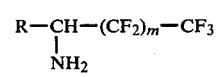

wherein R and m have the previously-given definitions either with a ω-halogeno lower alkyl isocyanate or isothiocyanate of the formula III $$A=C=N-(CH_2)n'-CH_2Hal \qquad (III)$$

wherein Hal is a chlorine, a bromine or an iodine atom

A is an oxygen or a sulphur atom and n' is an integer of 1 to 3 to produce a ω-halo lower alkyl Urea or thio Urea of the formula IV

wherein the substituents R, Hal, m and n' have the above-given definitions and A is an oxygen or a sulphur atom which is cyclised by warming into a compound of formula I'

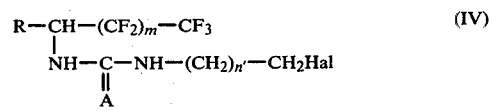

wherein

A is an oxygen or a sulphur atom

R is a lower alkyl or a lower cycloalkyl n and m have the above-given definitions which may, when desired, be salified by adding a mineral or organic acid or resolved into its optically-active isomers by salification with an optically-active organic acid either with a cyclic S-methyl isothioUrea of the formula V

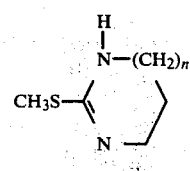 (V)

wherein n has the above-given definitions, in a strong polar medium to produce the compounds of formula I″

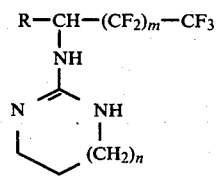 (I″)

wherein the substituents R, m and n have the above-given definitions which may be salified or resolved into its optically-active isomers or with an alkali-metal thiocyanate in the presence of an acylating agent to produce an acylthio urea of the formula VI

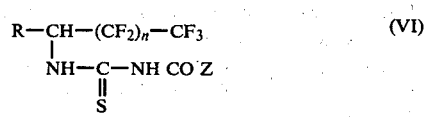 (VI)

in which R and n have the above-given definitions and Z is a lower alkyl radical, a phenyl radical, a substituted phenyl radical with one or two substituents selected from the group consisting of halogen atoms and lower alkoxy radicals, then saponifies the thus-formed N-acylthio Urea in a basic medium to produce the Thio Urea of the formula VII

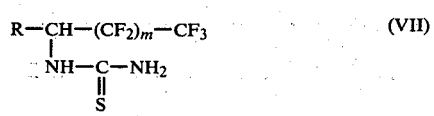 (VII)

wherein R and m have the above-given definitions, alkylates the latter by means of an alkylating salt to produce a thiouronium salt of the formula VIII

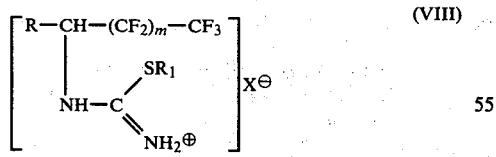 (VIII)

wherein R and m have the above-given definitions
$R_1$ is a lower alkyl radical
and X is a monovalent organic or mineral anion and condenses the latter with a lower alkylene diamine of the formula IX $$2HN-(CH_2)p-NH_2 \quad (IX)$$

wherein p is an integer of 2 to 4 to produce a compound of formula I″

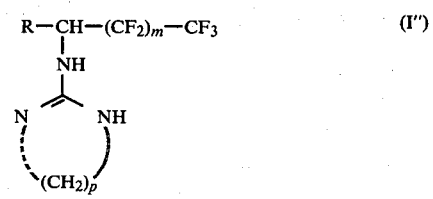 (I″)

wherein the substituents R, m and p have the above-given definitions, which may further be salified or resolved into their optically-active isomers.

According to this invention the process may also be defined by the following features which presently are the preferred ones:

(1) the condensation of the trifluoroethylamine of formula II with an isocyanate or thiocyanate of formula III is performed in an inert solvent such as a lower alkyl or a lower alkylene ether at a temperature of about 0° to about 10° C.

(2) the cyclisation of the ω-haloalkyl urea or thiourea of formula IV is carried out by warming it at a temperature ranging from 50° to 150°, preferably in an aqueous medium.

(3) this dehalohydration is performed in the presence or in the absence of a proton acceptor such as an alkali metal carbonate or a triloweralkylamine (4) the reaction between the trifluoroethylamine of formula II and the S-methyl isothiourea of formula V is performed in a polar solvent such as pyridine, dimethylformamide, dimethylacetamide or hexamethylphosphorotriamide and at a temperature ranging from 80° to 120°.

(5) the S-methylisothiourea of formula V is preferably used in the form of an acid addition salt giving rise to the production of an acid addition salt of a compound of the formula I″

(6) the alkali metal thiocyanate is ammonium thiocyanate (7) the acylating agent is preferably an acid halide and more preferably the acid chloride of a lower alkyl carboxylic acid benzoic acid or a substituted benzoic acid.

(8) the saponification of the S-acylthiourea of formula VI is performed by means of an alkali metal hydroxide such as sodium hydroxide or potassium hydroxide (9) the alkylating salt is preferably a lower alkyl halide, a lower alkyl sulphate, a lower alkyl arylsulphonate; the most preferred salts are methyl iodide or ethyl sulphate.

(10) the reaction between the thiouronium salt of formula VIII and the lower alkylene diamine of formula IX is performed by warming in a high boiling solvent such as pyridine, butanol or isopropanol

(11) the resolution of the compounds of formula I into their optically-active isomers is performed by salification using a chiral acid such as d-tartaric acid, ditoluyl d-tartaric acid, dibenzoyl d-tartaric acid, d-camphoric acid, NN-diethyl d-tartramic acid, d-glucose I-phosphoric acid, d-camphosulphonic acid or l-nerthoxyacetic acid.

The resolution may also be performed starting either from a compound of formula II or from an intermediate compound of formula IV, VI, or VII. The same resolving agents may be used as previously.

This invention also relates to another process for producing the compounds of formula II wherein R is a lower cycloalkyl having from 4 to 7 carbon atoms which comprises hydrogenating an unsaturated compound of formula X.

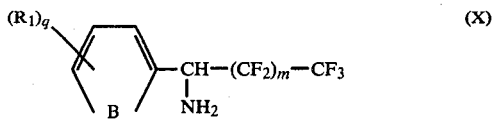

wherein B is a direct carbon-carbon bond, a methylene, a grouping CH=CH or —CH$_2$CH=CH—

$R_1$ is a hydrogen, a lower alkyl radical or a lower alkoxy radical m is zero or 1 q is zero or an integer of 1 to 3 in the presence of a metallic catalyst such as Raney Nickel, to produce the corresponding cycloalkyl derivative of formula II. Otherwise the compounds of formula II may be usually prepared starting from a trifluoromethyl ketone of the formula XII

wherein R and m have the above-specified meanings which is reacted with hydroxylamine to produce the corresponding ketoxime, reducing the latter into an amine of formula II by means of a metallic reducing agent, an alkali metal mixed hydride, or diborane.

The following examples are merely intended to illustrate the invention. They do not limit it in any manner.

EXAMPLE I dl 2-(α-trifluoromethyl ethylamino)oxazoline and its hydrochloride

Step A dl 1-(trifluoromethyl)ethylamine 9.1 g of lithium aluminohydride are dissolved in 180 ml ether and to this solution a solution of 15 g ααα-trifluoroacetone oxime in 100 ml ether are added portionwise over 30 minutes. The whole mixture is heated to reflux under inert atmosphere for one hour. After return to ambient temperature, excess of reagent is destroyed by adding an aqueous solution of sodium hydroxide. The ethereous phase is separated and dried on sodium sulphate then filtered. Hydrochloric acid is thereafter added until the pH value reaches about 2. The resulting hydrochloride precipitates is separated by succion-filtration, is washed with ether and dried under reduced pressure. 10 g of dl 1-(trifluoromethyl)ethylamine are recovered i.e. a yield of 57%.

1-(trifluoromethyl)methylamine is pure enough for the next step of the synthesis without further purification.

The starting material, ααα-trifluoroacetone-oxime, has been obtained according to the method disclosed by R. A. Shepard J. org. chem. 31 (1966) 964–965.

Step B

N-(β-chloroethyl) N'-[(1-trifluoromethyl)ethyl]urea 5 g of dl 1-(trifluoromethyl)ethylamine (hydrochloride) of step A are dissolved in 10 ml 2 N sodium hydroxide. The resulting solution of the free base is extracted three times with 10 ml ether. The united ethereous solutions are added to a solution of 3.1 g β-chloroethyl isocyanate in 5 ml ether. The mixture is cooled to about 0° until the addition is achieved. The mixture is thereafter kept under stirring for 12 hours while letting the reaction temperature reverting to 15°.

N-(β-chloroethyl) N'-[(1-trifluoromethyl)ethyl]urea progressively precipitates. The crystals are isolated, washed with cooled ether then dried under reduced pressure. 4.7 g of N-(β-chloroethyl) N'-[(1-trifluoromethyl)ethyl]urea are thus recovered i.e. a yield of 77%.

For analytical purpose the product is recrystallized from isopropyl ether. It melts at 108°–113° (with sublimation).

| Analysis: $C_6 H_{10} Cl F_3 N_2 O$ = 218.57 | | | | |
|---|---|---|---|---|
| | C | H | N | Cl % |
| Calculated | 32.96 | 4.61 | 12.81 | 16.25 |
| Found | 33.04 | 4.57 | 12.82 | 16.35 |

Step C dl 2-(α-trifluoromethyl ethylamino)oxazoline 3 g of N-(β-chloroethyl) N'-[(1-trifluoromethyl)ethyl]urea of step B are suspended in 20 ml water and 3.75 ml triethylamine. The reaction mixture is then heated to the reflux of the solvent for 3 hours then let to revert to room temperature. The aqueous phase is extracted three times with ether after acidification. The ethereous solutions are discarded and the remaining aqueous phase is made basic by adding ammonia until the pH value reaches 10. The alkaline solution is extracted with methylene chloride three times. The organic solutions are separated then united, washed with water, dried and evaporated off. 1.95 g of dl 2-(α-trifluoromethyl ethylamino)oxazoline are thus recovered.

The compound is further purified by sublimation under reduced pressure at 55° C. The pure compound melts at 102°–105° (sublim.)

| Analysis: $C_6 H_9 F_3 N_2O$ = 182.14 | | | |
|---|---|---|---|
| | C | H | N % |
| Calculated | 39.56 | 4.97 | 15.37 |
| Found | 39.31 | 4.96 | 15.29 | dl 2-(α-trifluoromethyl ethylamino)oxazoline is soluble in the dilute aqueous solutions of hydrochloric acid.

EXAMPLE II dl 2-[(1-trifluoromethyl 1-cyclopropyl)methylamino]oxazoline

Step A

Cyclopropyl trifluoromethyl ketone 1.5 g of magnesium turnings are suspended in 50 ml ether under nitrogen atmosphere. To this suspension few crystals of iodine are added, then dropwise a solution of 60.5 g of cyclopropyl bromide in 400 ml ether. The addition lasts about one hour. The reaction mixture is heated to reflux of the solvent for one hour.

A solution of the lithium derivative of trifluoroacetic acid is prepared by reacting 4 g sodium hydride with 50.5 g trifluoroacetic acid previously dissolved in 100 ml ether under bubbling of nitrogen and keeping the internal temperature at about 0° by immersing the flask in a cooling mixture of ice and salt.

The solution of lithium derivative is thereafter added to the solution of the magnesium derivative at room temperature. The reaction mixture is cooled during this addition in order to avoid any strong increase of the temperature.

After completion of the addition the reaction mixture is heated to reflux for 2 hours, then let to revert to about 20°. The excess of magnesium derivative is destroyed by cautious addition of 200 ml 6 N hydrochloric acid.

The organic phase is separated, washed with water and dried. The ether is evaporated off by fractional distillation. The viscous residue consisting of trifluoromethyl cyclopropyl ketone and tetrahydrofuran is used as such for the next step of the synthesis.

Step B

Cyclopropyl trifluoromethyl ketoxime

The viscous residue of step A is added to 3.49 g of hydroxylamine hydrochloride and 4.1 g anhydrous sodium acetate. The whole mixture is heated to reflux for 6 hours. The mixture is thereafter cooled in the refrigerator for a night. The resulting crystals are filtered, washed with water and dried under reduced pressure.

Cyclopropyl trifluoromethyl ketoxime boils at 55°–62° under 35 mm Hg.

| Analysis: $C_5H_6F_3NO = 153.09$ | | | |
|---|---|---|---|
| | C | H | N % |
| Calculated | 39.22 | 3.95 | 9.15 |
| Found | 39.57 | 3.93 | 8.79 |

Step C dl-(cyclopropyl trifluoromethyl)methylamine 9 g of the ketoxime of step B are reduced according to the procedure of example I step A. 7.3 g of dl cyclopropyl trifluoromethyl methylamine are obtained as the hydrochloride.

This compound melts at 235°–240°. The yield amounts to 71%.

| Analysis: $C_5H_8F_3N$—ClH = 175.58 | | | | |
|---|---|---|---|---|
| | C | H | N | Cl % |
| Calculated | 34.20 | 5.16 | 7.97 | 20.01 |
| Found | 34.39 | 5.30 | 7.94 | 20.17 |

Step D dl N-(β-chloroethyl) N'-[(cyclopropyl trifluoromethyl)methyl]urea

Using the experimental procedure of example I step B and starting from 3.6 g dl(cyclopropyl trifluoromethyl)-methylamine and β Chloroethyl isocyanate, 4.2 g β-chloroethyl urea as obtained (yield = 86%). The pure β-chloroethyl urea melts at 117°–121° (sublimation).

| Analysis: $C_8H_{12}ClF_3NO = 230.62$ | | | | |
|---|---|---|---|---|
| | C | H | N | Cl % |
| Calculated | 39.27 | 4.94 | 11.45 | 14.49 |
| Found | 39.44 | 5.04 | 11.36 | 14.41 |

Step E dl 2-[(α-trifluoromethyl cyclopropyl)methylamino]oxazoline 2.5 g of the β-chloroethyl urea of step D are cyclized into the oxazoline according to the procedure of example I step C. 1.55 g of dl 2-[(α-trifluoromethyl cyclopropyl)methylamino]oxazoline are obtained i.e. a yield of 78%. The so-obtained product melts at 113°–120° (sublim.) An analytical sample is obtained by sublimation under reduced pressure at about 80°. The pure product melts at 119°–121° (sublim.)

| Analysis: $C_8H_{11}F_3NO_2 = 208.19$ | | | |
|---|---|---|---|
| | C | H | N % |
| Calculated | 46.15 | 5.32 | 13.45 |
| Found | 46.21 | 5.19 | 13.39 |

The oxazoline is easily soluble in an aqueous solution of the just calculated amount of N/10 hydrochloric acid. Evaporating off the solvent allows the recovery of the dl 2-[(cyclopropyl trifluoromethyl)methylamino]oxazoline as the hydrochloride.

EXAMPLE III dl 2-(1-trifluoromethyl 3-methyl butylamino)oxazoline

Step A 4-methyl 1,1,1-trifluoropentanone

Using the same procedure as in example II step A starting from 164.4 g of 1-bromo 2-methyl propane, 35.6 g of 4-methyl 1,1,1-trifluoropentanone are obtained. It is a liquid boiling at 76°–84°
$N_D^{22} = 1.346$

Step B 4-methyl 1,1,1-trifluoropentanone oxime

Using the same procedure as in example II step B the title oxime is obtained with a yield of 72%. The compound is a liquid boiling at 74°–78° under 30 mm Hg.
$N_D^{24} = 1.3825$

Step C dl 1-trifluoromethyl 1-(2-methylpropyl)methylamine 25 g of the ketoxime of step B are reduced according to the procedure of example I step A. The yield amounts to 77%. The resulting amine is recovered as its hydrochloride MP = 150°–157° (sublim)

| Analysis $C_6H_{12}F_3N\,ClH = 191.64$ | | | | |
|---|---|---|---|---|
| | C | H | N | Cl % |
| Calculated | 37.60 | 6.23 | 7.31 | 18.50 |
| Found | 37.54 | 6.47 | 7.30 | 18.58 |

Step D dl N-(β-chloroethyl) N'-[1-trifluoromethyl 1-(2-methylpropyl)methyl]Urea Using the same procedure as in example I step B and starting from 7 g dl 1-trifluoromethyl 1-(2-methylpropyl)methylamine (hydrochloride), the β-chloroethyl Urea is obtained with a yield of 94%.

The β-chloroethyl Urea melts at 63°–67°. A further recrystallization from pentane increases the melting point to 64°–67°

| Analysis $C_9H_{16}ClF_3N_2O = 260.67$ | | | | |
|---|---|---|---|---|
| | C | H | N | Cl % |
| Calculated | 41.46 | 6.18 | 10.74 | 13.60 |

-continued

| Analysis $C_9H_{16}ClF_3N_2O = 260.67$ | | | |
|---|---|---|---|
| | C | H | N | Cl % |
| Found | 41.16 | 6.10 | 10.73 | 13.69 |

Step E dl 2-(1-trifluoromethyl 3-methylbutylamino)oxazoline

Using the same procedure of example I step C and starting from 8 g of the β-chloroethyl Urea of step D, 5.7 g of dl 2-(1-trifluoromethyl 3-methylbutylamino)oxazoline are produced i.e. a yield of 85%

For analytical purposes a sample is further purified by subliming it at 55°–60°. The analytical compound melts at 81°–85° (sublim). dl 2-(1-trifluoromethyl 3-methylbutylamino)oxazoline is soluble in dilute hydrochloric acid. By evaporating off the solvent, the hydrochloride is obtained.

| Analysis $C_9H_{15}F_3N_2O = 224.22$ | | | |
|---|---|---|---|
| | C | H | N % |
| Calculated | 48.20 | 6.74 | 12.49 |
| Found | 48.11 | 6.80 | 12.40 |

EXAMPLE IV

2-[(1-trifluoromethyl 1-cyclohexyl)methylamino]oxazoline (dextrorotatory isomer)

Step A

α-trifluoromethyl cyclohexylmethylamine (laevorotatory isomer)

In a sealed vessel they are introduced 8.2 g α-trifluoromethyl benzylamine (dextrorotatory isomer) about 1 g to 2 g Raney Nickel and 180 ml ethyl acetate. The reaction mixture is hydrogenated at 110° for 4 hours under 180 bars then let to revert to room temperature. The catalyst is separated by succion-filtration and rinsed with few ml ethyl acetate. The organic solutions are united, added to a saturated ethereous solution of hydrochloric gas. The hydrochloride of α-trifluoromethyl cyclohexyl methylamine precipitates. After isolation it is washed with ether and dried under reduced pressure. 9.6 g of the hydrochloride are thus obtained i.e. a yield of 94%. The hydrochloride is converted into the free base by adding a basic solution α-trifluoromethyl cyclohexyl methylamine is further purified by fractional distillation.

| 7 g of the pure compound are recovered BP = 80°/18mmHg $N_D^{24} = 1.4185$ | |
|---|---|
| $[\alpha]_D$ in ethanol (C = 1%) | |
| λ (mµ) | $[\alpha]^{24}$ |
| 578 | −18° |
| 546 | −20°6 |
| 436 | −35°5 |
| 365 | −56°8 |

Step B

N-(β-chloroethyl) N'-(α-trifluoromethyl cyclohexyl methyl)Urea (dextrorotatory isomer)

Using the same procedure as in example I step B and starting from 3.5 g of α-trifluoromethyl cyclohexyl methylamine of step A 4.6 g of the resulting β-chloroethyl Urea are recovered (i.e. a yield of 85%). This compound melts at 135°–140° ( with sublim.)

| Analysis $C_{11}H_{18}ClF_3N_2O = 286.73$ | | | |
|---|---|---|---|
| | C | H | N | Cl % |
| Calculated | 46.07 | 6.82 | 9.77 | 12.36 |
| Found | 45.87 | 6.07 | 9.67 | 12.53 |

| rotatory power (ethanol C = 5%) | |
|---|---|
| λ mµ | $[\alpha]^{24}$ |
| 578 | +3°1 |
| 546 | +3°6 |
| 436 | +6°6 |
| 365 | +11°4 |

Step C

2-[(1-trifluoromethyl 1-cyclohexyl)methylamino]oxazoline (dextrorotatory isomer)

Starting from 3.5 g of the β-chloroethyl Urea of step B, 2.15 g of 2[(1-trifluoromethyl 1-cyclohexyl)methylamino]oxazoline are obtained according to the procedure of example I step C (i.e. a yield of 70%). The so-obtained compound melts at 103°–107° (sublim.). The product is purified by sublimation. The melting point is increased to 104°–107°

| Analysis $C_{11}H_{17}F_3N_2O = 250.25$ | | | |
|---|---|---|---|
| | C | H | N % |
| Calculated | 52.79 | 6.84 | 11.19 |
| Found | 52.94 | 6.70 | 11.04 |

| rotatory power (ethanol C = 1%) | |
|---|---|
| λ mµ | $[\alpha]^{22}$ |
| 578 | +28°2 |
| 546 | +32°4 |
| 436 | +57°6 |
| 365 | +96°2 |

2[(1-trifluoromethyl 1-cyclohexyl)methylamino]oxazoline is soluble in dilute hydrochloric acid giving rise to the formation of the hydrochloride.

The starting material α-trifluoromethyl benzylamine (dextrorotatory isomer) is produced according to the process disclosed in the French Pat. No. 2,358,890 (to Science Union).

The starting material may also be obtained according to a process which consists in reacting cyclohexyl bromide with magnesium to produce the cyclohexyl magnesium bromide, condensing it with trifluoroacetic acid to form cyclohexyl trifluoromethyl ketone according to the method disclosed by F. E. Horkes J. Org. Chem. 32 (1967) 1311–1318.

Cyclohexyl trifluoromethyl ketone is further converted into its ketoxime which is hydrogenated into (1-trifluoromethyl 1-cyclohexyl)methylamine. The latter is resolved into their optically active isomers by means of salification with d-tartaric acid, or dibenzoyl d-tartaric acid.

EXAMPLE V

2-[(1-trifluoromethyl 1-cyclohexyl)methylamino]oxazoline (laevorotatory isomer)

Using the same procedure as in example IV and starting from α-trifluoromethyl benzylamine (laevorotatory isomer) they are successively produced:

-α-trifluoromethyl cyclohexyl methylamine (dextrorotatory isomer)
rotatory power ethanol C = 1%

| λ mμ | $[α]^{22}$ |
|---|---|
| 578 | +16°7 |
| 546 | +19° |
| 436 | +38°5 |
| 365 | +51°5 |

-N—(β-chloroethyl) N'—(1-trifluoromethyl 1-cyclohexyl methyl) Urea (laevorotatory isomer)
rotatory power (ethanol C = 5%)

| λ mμ | $[α]^{22°5}$ |
|---|---|
| 578 | −3°3 |
| 546 | −3°8 |
| 436 | −7°1 |
| 365 | −12°3 |

-2-[(1-trifluoromethyl 1-cyclohexyl) methylamino] oxazoline (laevorotatory isomer)
melting point 104–107° (sublim.)
rotatory power (ethanol C = 1%)

| λ μ | $[α]^{22}$ |
|---|---|
| 578 | −28°2 |
| 546 | −32°4 |
| 436 | −58°1 |
| 365 | −96°3 |

Analysis $C_{11}H_{17}F_3N_2O$ = 250.25

| | C | H | N % |
|---|---|---|---|
| Calculated | 52.79 | 6.84 | 11.19 |
| Found | 52.82 | 6.76 | 10.95 |

EXAMPLE VI

2-[(1-trifluoromethyl 1-cyclohexyl)methylamino]imidazoline (laevorotatory isomer)

Step A

N-[(1-cyclohexyl 1-trifluoromethyl)methyl]thio Urea 12.3 g ammonium thiocyanate are dissolved in 80 ml acetone and to this solution 11.25 ml benzoyl chloride are portionwise added in 15 mn. The mixture is heated to reflux. This solution kept at the reflux temperature is added to a solution of 27.8 g (1-trifluoromethyl 1-cyclohexyl)methylamine (dextrorotatory isomer) in 100 ml acetone. The mixture is further heated for 2 hours. The solvent is distilled and the dry residue is taken up in 25 ml methylene chloride. The methylenic solution is washed with water until free of chlorides then evaporated off. The oily residue weighs 47.5 g. The so-formed N-benzoyl derivative is thereafter saponified by 150 ml 2 n-sodium hydroxide and 250 ml ethanol at room temperature for 24 hours.

Ethanol is distilled off and the residue is taken up in ether. The organic solution is washed until the washings are neutral (pH about 7.8). The organic phase is dried and evaporated off. 23 g N-[(1-cyclohexyl 1-trifluoromethyl)methyl]thio Urea are recovered i.e. a yield of 75%.

The compound is used a such for the next step of the synthesis.

Step B

N-[(1-cyclohexyl 1-trifluoromethyl)methyl]methyl isothio uronium iodide (laevorotatory isomer)

27 g of the thio Urea of the step A are dissolved in 150 ml acetone and 15 ml methyl iodide are added to. The mixture is heated to reflux for 4 hours then evaporated to dryness. 41 g of crystalls are recovered which melts at 160°–170° (dec.). For the analysis they are recrystallized from acetonitrile. 34.3 g of pure compound are obtained (i.e. a yield of 78%). The compound melts at 170° (dec.)

Analysis $C_{10}H_{17}F_3N_2S,HI$ = 350.16

| | C | H | N | S % |
|---|---|---|---|---|
| Calculated | 31.41 | 4.75 | 7.32 | 8.32 |
| Found | 31.67 | 4.73 | 7.89 | 8.19 | rotatory power (ethanol C = 1%)

| λ mμ | $[α]^{22}$ |
|---|---|
| 578 | −3°1 |
| 546 | −3°7 |
| 436 | −7°6 |
| 365 | −13°7 |

Step C

2-[(1-trifluoromethyl 1-cyclohexyl)methylamino]imidazoline (dextrorotatory isomer)

21 g of the isothio uronium iodide of step B are mixed with 3 ml ethylene diamine in 270 ml iso amyl alcohol and heated to reflux for 6 hours. The solution is let to revert to room temperature and evaporated off. The residue crystallized by cooling, essentially consisting in the 2-[(1-trifluoromethyl 1-cyclohexyl)methylamino]imidazoline, hydroiodide.

After 12 hours cooling in a refrigerator, the crystals are separated and dried. They are taken up in 120 ml N-sodium hydroxide and 100 ml ethanol. The mixture is kept aside for 12 hours at room temperature and the free base is thereafter extracted with methylene chloride.

After having the methylene chloride evaporated off, 6.3 g 2-[(1-trifluoromethyl 1-cyclohexyl)methylamino]imidazoline are obtained which melts at 148°–157° (sublim.). A further crystallization from heptane provides a pure compound having a melting point of 154°–157°

Analysis $C_{11}H_{18}F_3N_2$ = 235.18

| | C | H | N % |
|---|---|---|---|
| Calculated | 52.99 | 7.28 | 16.25 |
| Found | 53.00 | 7.33 | 16.59 |

EXAMPLE VII

2-[(1-trifluoromethyl 1-cyclohexyl)methylamino]tetrahydropyrimidine (dextro rotatory isomer)

Using the same procedure as in example VI but using 2 ml 85 propylene diamine instead of ethylene diamine, 2-[(1-trifluoromethyl 1-cyclohexyl)methylamino]tetrahydropyrimidine (dextro rotatory isomer) is obtained.

EXAMPLE VIII

2-[(1-trifluoromethyl 1-cyclohexyl)methylamino]thiazoline (dextro rotatory isomer)

7.1 g of 1-trifluoromethyl 1-cyclohexyl methylamine (dextro rotatory isomer) and 26 g 2-methylthio thiazoline as the hydroiodide are dissolved in 75 ml dimethyl formamide. The solution is heated to reflux for one hour then let to revert to room temperature. The reaction mixture is thereafter diluted with an equal colume of isopropyl ether. The crystallization is initiated by scratching and the mixture is kept aside in a cool place for a night.

The 2-[(1-trifluoromethyl 1-cyclohexyl)methylamino]thiazoline as the hydroiodide is separated by filtration, dried, washed with few ml of isopropyl ether and troughly dried.

The hydroiodide is taken up in water then converted into the free base by adding a solution of soda until frank basicity. The aqueous solution is extracted several times with isopropyl ether. The organic phases are united, washed with water, dried, filtered and evaporated off.

2-[(1-trifluoromethyl 1-cyclohexyl)methylamino]-thiazoline (dextro rotatory isomer) is thus obtained which melts at 135°–138° after having recrystallized it from acetonitrile.

| Analysis $C_{11}H_{16}F_3N_2S$ = 265.29 | | | | |
|---|---|---|---|---|
| | C | H | N | S % |
| Calculated | 50.75 | 4.26 | 10.77 | 12.32 |
| Found | 50.60 | 4.37 | 10.83 | 12.75 |

EXAMPLE IX

2[(1-pentafluoroethyl 1-cyclohexyl)methylamino]oxazoline (dextro rotatory isomer)

Using the same procedure as in example II and starting from pentafluoropropiophenone (obtained according to K. T. Duhart J. of Am. Chem. Soc. 78 (1956) 2268), the following compounds are produced:
- pentafluoropropiophenone oxime MP 53° and 70° (i.e. a yield of 75%)
- dl α-phenyl(pentafluoropropyl)amine BP=82°–90°/18 mmHg the yield amounts to 70%
- dl α-phenyl(pentafluoropropyl)amine, hydrochloride MP=178°–186°
- dl[1-cyclohexyl 1-(pentafluoroethyl)]methylamine
- [1-cyclohexyl 1-(pentafluoroethyl)]methylamine (dextro rotatory isomer)
- N-[1-cyclohexyl 1-(pentafluoroethyl)methyl]N'-(-chloroethyl)Urea (dextro rotatory isomer)
- 2-[(1-cyclohexyl 1-pentafluoroethyl)methylamino]oxazoline (dextro rotatory isomer) which melts at 141°–143° (from isopropanol)

EXAMPLE X dl 2-[(1-pentafluoroethyl 1-cyclohexyl)methylamino]oxazoline

Using the same procedure as in example IX but avoiding the resolution step, dl 2-[(1-pentafluoroethyl-1-cyclohexyl)methylamino]oxazoline is obtained. It melts at 115°–118°. This compound is soluble in N/10 hydrochloric acid solutions.

| Analysis $C_{12}H_{17}F_3N_2O$ = 302.26 | | | |
|---|---|---|---|
| | C | H | N % |
| Calculated | 48.18 | 5.89 | 9.09 |
| Found | 47.99 | 5.70 | 9.33 |

EXAMPLE XI

2-[(1-trifluoromethyl 1-cyclohexyl)methylamino]tetrahydropyrimidine (laevorotatory isomer)

Using the same procedure as in example VI and starting from α-trifluoromethyl cyclohexyl methylamine from example V step A, 2-[(1-trifluoromethyl 1-cyclohexyl)methylamino]tetrahydropyrimidine (laevorotatory isomer) is obtained.

The pure compound melts at 170°–178° (sublim.) after recrystallization from acetonitrile. It is soluble in N/10 hydrochloric acid solutions giving rise to the production of the hydrochloride.

| Rotatory power (ethanol C = 1%) | |
|---|---|
| λ mμ | $[\alpha]^{18°}$ |
| 578 | −18°2 |
| 546 | −21°2 |
| 436 | −39°7 |

| Analysis: $C_{12}H_{20}F_3N_3$ = 263,30 | | | |
|---|---|---|---|
| | C | H | N % |
| Calculated | 54,73 | 7.65 | 15.96 |
| Found | 54.40 | 7.87 | 15.82 |

EXAMPLE XII dl 2-[(trifluoromethyl 1-(4'-methylcyclohexyl-1')methylamino]oxazoline Using the procedure of example IV and starting from p.bromotoluene they are successively produced:
- p-methyl ααα-trifluoro acetophenone
- p-methyl ααα-trifluoro acetophenone ketoxime
- dl(p-methyl phenyl)ααα-trifluoroethylamine
- dl[(4-methylcyclohexyl) 1-trifluoromethyl]methylamine (mixture of diastereoisomers)
- dl N-[(4-methylcyclohexyl-1) 1-trifluoromethyl]methyl N'-(2-chloroethyl)urea
- dl 2-[1-(4'-methylcyclohexyl-1') 1-trifluoromethyl]amino oxazoline (mixture of diastereoisomers) melting at 94°–102° (sublim.)

| Analysis: $C_{12}H_{19}F_3N_2O$ = 264.47 | | | |
|---|---|---|---|
| | C | H | N % |
| Calculated | 54.49 | 7.24 | 10.59 |
| Found | 54.51 | 7.14 | 10.46 |

EXAMPLE XIII

Pharmacological study of the compounds of formula I (a) determination of the acute toxicity The average letal dosis ($LD_{50}$) is determined on batches of 10 mice (swiss strain) weighing about 20 g, by intraperitonal injections of increasing doses of the compounds to be tested.

The animals are kept under survey for 8 days and the deaths, if any, are numbered. The lethal dosis is graphically determined according to the method of Tainter and Miller.

The compounds of general formula I have been injected at doses ranging from 20 to 200 mg/Kg. In general the lethal dosis is about 100 mg/kg. The only manifestations of toxicity in the animals are sedation and pilo-erection.

(b) determination of the hypotensive activity

The compounds of general formula I have been tested for hypotensive activity in lots of dogs, previously anesthetized with intravenous Nembutal, which received the compound to be tested at doses ranging from 0.005 to 0.5 mg/Kg by intravenous way. At the lowest doses (5γ and 10γ/Kg) the decrease of the mean arterial pressure is only shortlasting but the cardiac rhythm is significantly decreased for a period of about 30 mn.

Higher doses induce at first a slight increase of the arterial pressure then a significant decrease. The cardiac rhythm is decreased and this decrease may be as high as 50% of the normal cardiac rhythm as observed in the controls.

(c) search of a neurological effect

In the mice (strain CD) doses of 10 and 20 mg/Kg through intraperitoneous way induce only a decrease of the motility, a decrease of the body temperature, a decrease in the food and drink intake.

In the rats (strain LE), small doses induce a state of excitation, and pilo-erection. Higher doses induce a decrease of the motility and of the muscular tone.

In the cats the administration of the compounds induce at first excitation then a weak depressive state.

Therefore the compounds of general formula I appear to be stimulant agent of the central noradrenergic receptors and they cause an inhibition of the sympathic tone, hypotension and brady cardia. They are active parenterally as well as per oral way.

EXAMPLE XIV

Tablets containing 1 mg of active ingredient 2-[(1-trifluoromethyl 1-cyclohexyl)methylamino]oxazoline (laevorotatory isomer)

| Wheat starch | 40 g |
|---|---|
| Mais starch | 15 g |
| Magnesium stearate | 20 g |
| Magnesium silicate | 15 g |
| Colloidal silica | 7.5 g |
| Ethyl cellulose | .2 g |
| polyvinyl pyrrolidone | 4 g | for 1000 tablets weighing each about 0.100 g.

What we claim is:
1. An oxazoline having the formula $I_A$

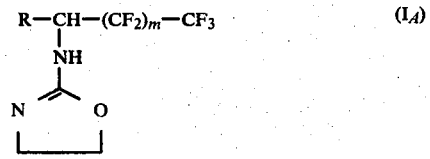

wherein
R is a $C_1$ to $C_6$-alkyl or a cycloalkyl having 4 to 7 carbon atoms or a substituted $C_4$ to $C_7$-cycloalkyl, the substituents of which are selected from the group consisting of loweralkyl and loweralkoxy, and
m is zero or 1, and
the optically-active isomer or a diastereoisomer of such Formula $I_A$ compound, or an acid addition salt of such a compound.

2. A method for treating hypertension in hypertensive patients which consists in administering to mammals suffering from hypertension a safe but effective amount of a compound of claim 1 or a salt thereof, for eliciting said condition.

3. The method of claim 2 in which the safe but effective amount of a compound of claim 1 or a salt thereof ranges from 0.1 mg to 5 mg daily in the man.

4. A compound according to claim 1, wherein R is a cycloalkyl radical having 5 to 7 carbon atoms.

5. A compound according to claim 1 which is dl 2-[(1-trifluoromethyl-3-methyl)butylamino]oxazoline and its hydrochloride.

6. A compound according to claim 1 which is dextrorotatory 2-[(1-trifluoromethyl 1-cyclohexyl)methylamino]oxazoline.

7. A compound according to claim 1 which is laevorotatory 2-[(1-trifluoromethyl 1-cyclohexyl)methylamino]oxazoline.

8. A compound according to claim 1 which is 2-[(1-trifluoromethyl)(4'-methylcyclohexyl-1')methylamino]oxazoline.

9. A pharmaceutical composition in dosage unit form, useful for treating hypertension in a mammal suffering therefrom, which comprises an amount of a compound of claim 1 effective for treating hypertension, mixed with a pharmaceutically-acceptable carrier or vehicle.

10. A pharmaceutical composition according to claim 9 in which the carrier or vehicle is that suitable for the oral, parenteral, permucous, perlingual or rectal routes of administration.

11. A pharmaceutical composition according to claim 9 in which the amount of active ingredient of claim 4 or a salt thereof ranges from 0.1 mg to 2 mg per unit dosage.

* * * * *